United States Patent

Watts et al.

[11] Patent Number: 5,965,805
[45] Date of Patent: Oct. 12, 1999

[54] APPARATUS AND METHOD FOR DETERMINING THE AIR ENTRAINMENT CHARACTERISTICS OF LIQUIDS

[75] Inventors: Raymond F. Watts, Long Valley; Manoj Tandon, Princeton; Patrick J. Colby, Piscataway, all of N.J.

[73] Assignee: Exxon Chemical Patents Inc., Linden, N.J.

[21] Appl. No.: 08/940,255

[22] Filed: Sep. 30, 1997

[51] Int. Cl.$^6$ .............................. G01N 7/00; G01N 33/26
[52] U.S. Cl. .................. 73/53.01; 73/19.11; 73/53.05
[58] Field of Search ............... 73/19.01, 19.05, 73/19.1, 19.11, 19.12, 53.01, 53.05, 60.11, 61.41, 64.44

[56] References Cited

U.S. PATENT DOCUMENTS

| | | |
|---|---|---|
| 2,406,179 | 8/1946 | Walsh et al. . |
| 3,381,518 | 5/1968 | Loehle . |
| 4,395,902 | 8/1983 | Espenscheid et al. . |
| 4,763,514 | 8/1988 | Naito et al. . |
| 5,243,848 | 9/1993 | Cox et al. ............................. 73/19.05 |

FOREIGN PATENT DOCUMENTS

| | | |
|---|---|---|
| 53-72680 | 6/1978 | Japan . |
| 54-47041 | 4/1979 | Japan . |
| 63-277954 | 11/1988 | Japan . |
| 2108944 | 4/1990 | Japan . |
| 2245636 | 10/1990 | Japan . |
| 0905739 | 2/1982 | U.S.S.R. . |
| 1239294 | 6/1986 | U.S.S.R. . |
| 2081896 | 2/1982 | United Kingdom . |

OTHER PUBLICATIONS

G.E. Totten et al., "Hydraulic Fluids: Foaming, Air Entrainment, and Air Release—A Review" in SAE Technical Paper Series No. 972789, pp. 53–63 (International Off–Highway Powerplant Congress & Exposition, Sep. 8–10, 1997), reprint from Trend and Developments of Fluid Power for Off–Highway Applications.

*Primary Examiner*—Michael Brock

[57] ABSTRACT

Described is an apparatus and a method to accurately determine the gas entrainment characteristics of liquids, such as automatic transmission fluids. The apparatus comprises a liquid reservoir, a conduit having an inlet and an outlet connected to the liquid reservoir so as to form a pressurized recirculating loop for the liquid in the liquid reservoir, a pump for moving the liquid through the conduit, and a means for admitting gas (such as air) into the conduit to aerate the liquid.

17 Claims, 2 Drawing Sheets

5,965,805

APPARATUS AND METHOD FOR DETERMINING THE AIR ENTRAINMENT CHARACTERISTICS OF LIQUIDS

BACKGROUND OF THE INVENTION

This invention pertains to an apparatus and a method for determining the gas entrainment characteristics of liquids, such as lubricating compositions, particularly automatic transmission fluids (ATFs).

The intermixing of a lubricant and air results in the formation of a gas-in-liquid dispersion. Such gas-in-liquid dispersions are technically termed "foams" (see for example: Perry's Chemical Engineers' Handbook, Sixth Edition, McGraw-Hill Co., New York, 1984, Chapter 18). In the lubricant art, the terms air "entrainment" and "foaming" are commonly applied to describe the processes of air incorporation into, and release from, lubricants, respectively. The formation of a stable air-in-oil dispersion in a lubricant under pressure is commonly referred to as "air entrainment", whereas foaming is normally understood to mean the release of dispersed air from a liquid phase at atmospheric pressure. The bubble rich layer which forms on top of the liquid phase is referred to as "foam." Foaming, as used in this context, is the result of poor release of air from the liquid phase. Normally, an air-in-oil dispersion, a lubricant with entrained air formed under pressure, will foam when the pressure is released and the dispersion is returned to atmospheric pressure.

Foaming is a function of the interfacial tension of the dispersion and the viscosity of the liquid phase. Air entrainment, as was previously noted, is the ability of the lubricant to form a stable air-in-oil dispersion under pressure. Air entrainment characteristics are influenced by the interfacial tension of the dispersion (as are foaming characteristics), and are also highly dependent on the size of the bubbles formed and the ability of the lubricant to stabilize the bubbles either through viscous isolation or additive adsorption. The amount of air that can be entrained by a lubricant is controlled by many factors, as indicated above. What is of interest is that lubricants vary in the maximum amount of air that they can entrain irrespective of the volume of air introduced into them. The ability to determine this maximum air entrainment capacity of a lubricant is the subject of this invention.

In many lubrication applications air and the lubricant are mixed together at high shear rates and at high temperatures. These conditions cause formation of air-in-oil dispersions. Entrained air in lubricants is detrimental to performance for several reasons. First it disrupts the lubricant film, thereby leading to wear. Second, air in intimate contact with the lubricant under pressure and at elevated temperatures causes oxidation. And third, air is compressible so hydraulic fluids with entrained air give soft or "spongy" responses. Transmissions (manual, automatic or continuously variable) are particularly susceptible to air entrainment. These devices have rotating elements that dip into the lubricant and in the process effectively mix air into the lubricant. Transmissions of this type also have pumps such that any air drawn into the pump will be dispersed into the lubricant phase. This aerated fluid then is subject to the problems previously described.

Many apparatuses and tests are known for determining the foaming characteristics of lubricants, including the ASTM D-892 Standard Test Method for Foaming Characteristics of Lubricating Oils, and the General Motors DEXRON®-III Foam Test, GM-6297M. However, there are no such apparatuses or procedures for determining the air entrainment characteristics of lubricants.

The present invention provides an apparatus and a method to accurately determine the gas entrainment characteristics of liquids, such as new or used lubricants, particularly automatic transmission fluids.

SUMMARY OF THE INVENTION

The apparatus of this invention comprises a liquid reservoir, a conduit having an inlet and an outlet connected to the liquid reservoir so as to form a recirculating loop for the liquid in the liquid reservoir, a pump for moving the liquid through the conduit, and a means for admitting gas into the conduit.

This invention also concerns a method for determining the gas entrainment characteristics of a liquid comprising recirculating the liquid from a reservoir through a conduit by a pump, injecting gas into the conduit to mix with the recirculating liquid, and sampling the liquid.

DETAILED DESCRIPTION OF THE INVENTION

In one embodiment of this invention, the apparatus has a pressure control valve downstream from the pump to control the pressure in a portion of the conduit between the pump and the valve. Downstream is defined as being after the flowing liquid has passed a reference point, e.g. the pump, and upstream is defined as being before the flowing liquid has reached a reference point. Thus, downstream from the pump is at some point along the flow of liquid coming out of the pump; whereas upstream of the pump is at some point along the flow of the liquid going into the pump.

In yet another embodiment the apparatus has a sampling valve. In a preferred embodiment the sampling valve is a solenoid valve being controlled by a timer disposed downstream from the pump and upstream from the pressure control valve.

In yet another embodiment the apparatus includes a means to heat the liquid.

In another preferred embodiment the pump is a vane pump.

In yet another embodiment the conduit comprises two outlets, the first of which discharges liquid above the surface of the liquid in the liquid reservoir, and the second of which discharges liquid below the surface of the liquid in the liquid reservoir immediately next to the inlet of the conduit.

In a preferred embodiment the apparatus includes a metered air injection system disposed immediately upstream of the pump.

In another embodiment the liquid is recirculated at a controlled temperature, and a controlled pressure above atmospheric pressure through a portion of the conduit.

In another preferred embodiment the liquid is sampled downstream from the pump at predetermined intervals.

The types of liquids whose gas entrainment characteristics can be investigated according to the present invention include all liquids susceptible to gas entrainment, including but not limited to lubricant base oils, hydraulic oils, automatic transmission fluids, manual transmission fluids, continuously variable transmission fluids, internal combustion engine oils, gear oils, turbine lubricating oils and electrical transformer cooling oils. Preferably, the liquid is an automatic transmission fluid.

Any gas which is inert to the liquid being pumped may be used. Thus, nitrogen or carbon dioxide may be useful, although in the examples described, air was used.

DESCRIPTION OF THE DRAWINGS

Figure 1:
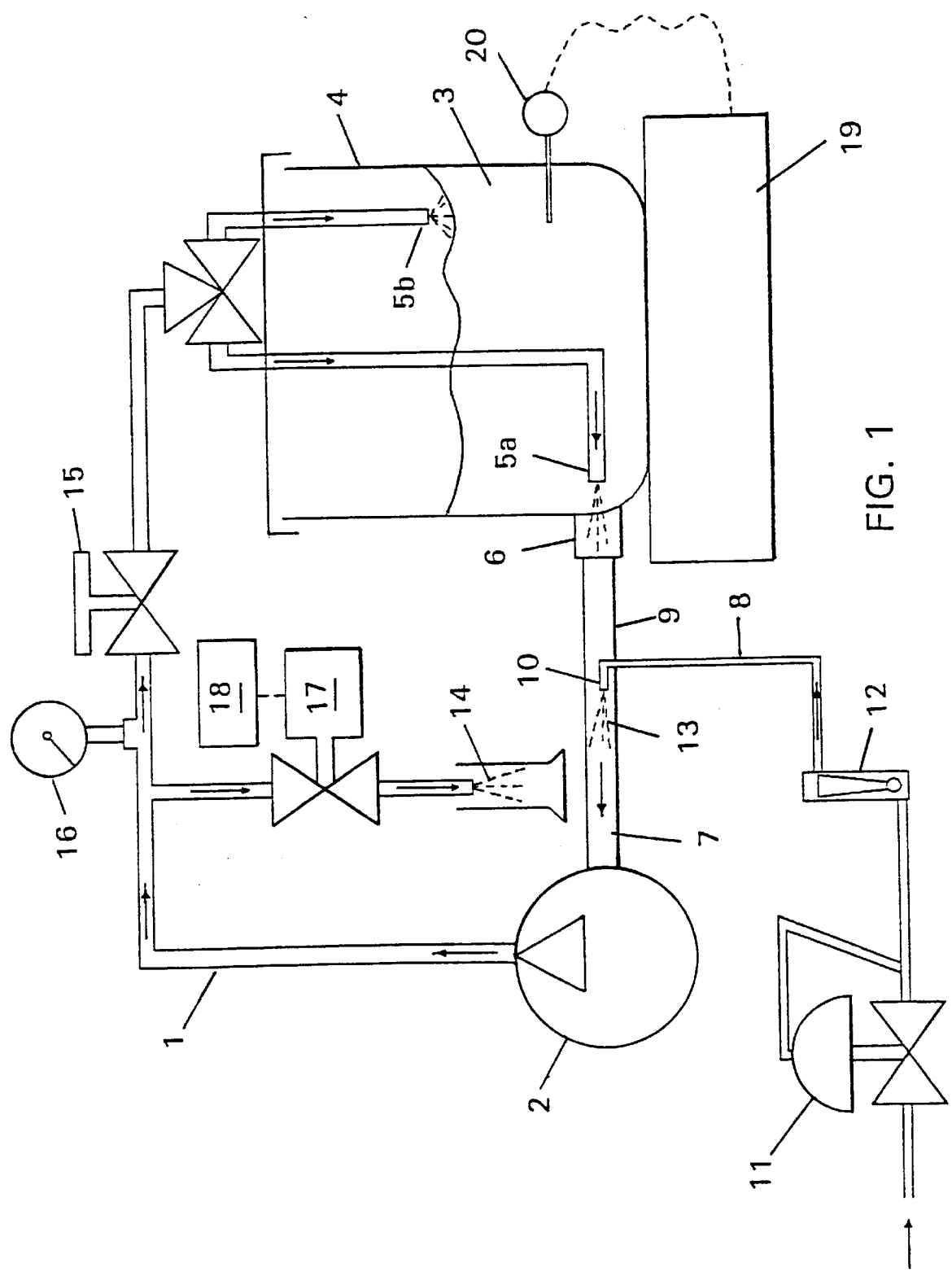
FIG. 1 is a schematic illustration of an embodiment of an apparatus according to this invention.

The apparatus shown as FIG. 1, comprises a heated reservoir fitted with a conduit (1), that forms a recirculating loop, and a vane pump (2). In the embodiment illustrated in the drawing, the apparatus is designed to simulate the air entrainment mechanism of an automatic transmission. A heated volume of fluid (3) is circulated from a reservoir (4), through the conduit in a recirculating loop by vane pump (2). A first conduit outlet (5-a) is placed in very close proximity to inlet (6) of the conduit leading to the pump. A second outlet (5-b) of the conduit is placed above the surface of the liquid in the liquid reservoir. The first conduit outlet is in close proximity to the inlet of the pump allowing for recirculation of the aerated lubricant.

Immediately adjacent to the inlet of the pump (7), a metered quantity of air (8) is injected into fluid stream (9) (at the suction inlet of the pump) via sparger (10). The air inlet system is controlled so as to meter air into the lubricant stream at a predetermined rate. Air flow rate is controlled by air regulator (11) and air flow is controlled by rotameter (12). The aerated fluid (13) is recirculated until an equilibrium is established and then a sample of aerated fluid (14) is withdrawn and the volume of air measured.

The volume of air is calculated by noting the difference in the liquid level immediately after collection and after all air has escaped from the liquid.

The conduit is fitted with restricting valve (15) to allow a portion of the conduit to operate at high pressure. A pressure gauge (16) is also fitted upstream from the restricting valve and downstream from the pump. Sampling valve (17) is fitted to the conduit on the high pressure side of the restricting valve to allow for sample collection. The sample collection valve is a solenoid valve which is operated by timer (18). Fluid samples are collected into a graduated cylinder by opening the sample collection valve for a predetermined interval, e.g. 2 seconds. As evidenced by the standard deviations in Table 1, such a time based sampling method is more accurate and more reproducible than a volume based sampling method, e.g. expelling 500 cc's of mixture. Upon collection of the sample the volume of sample is immediately recorded, and then the volume of the liquid is again recorded when all air has been released from the system. The difference in the two figures is the volume of air entrained.

The liquid may be heated by hot plate (19) under the reservoir and the temperature is monitored by temperature probe (20) in contact with the liquid.

Other methods of temperature control, such as, heating or cooling coils within the reservoir, and an external jacket on the reservoir through which a heating or cooling liquid is circulated may also be used. Optionally, the apparatus may be operated at ambient temperature.

The apparatus may be constructed from any material capable of holding the lubricant to be evaluated, e.g. stainless steel, carbon steel. The size of the apparatus and capacities of individual components may be any size and any capacity to hold the lubricant being evaluated, and may also be scaled to simulate a desired system. For example, reservoir capacity of 2 to 25 liters may be used; pump capacity of 5 to 25 liters per minute may be used, and air flow rate of 0.1 to 1.0 liters per minute may be used.

Figure 2:
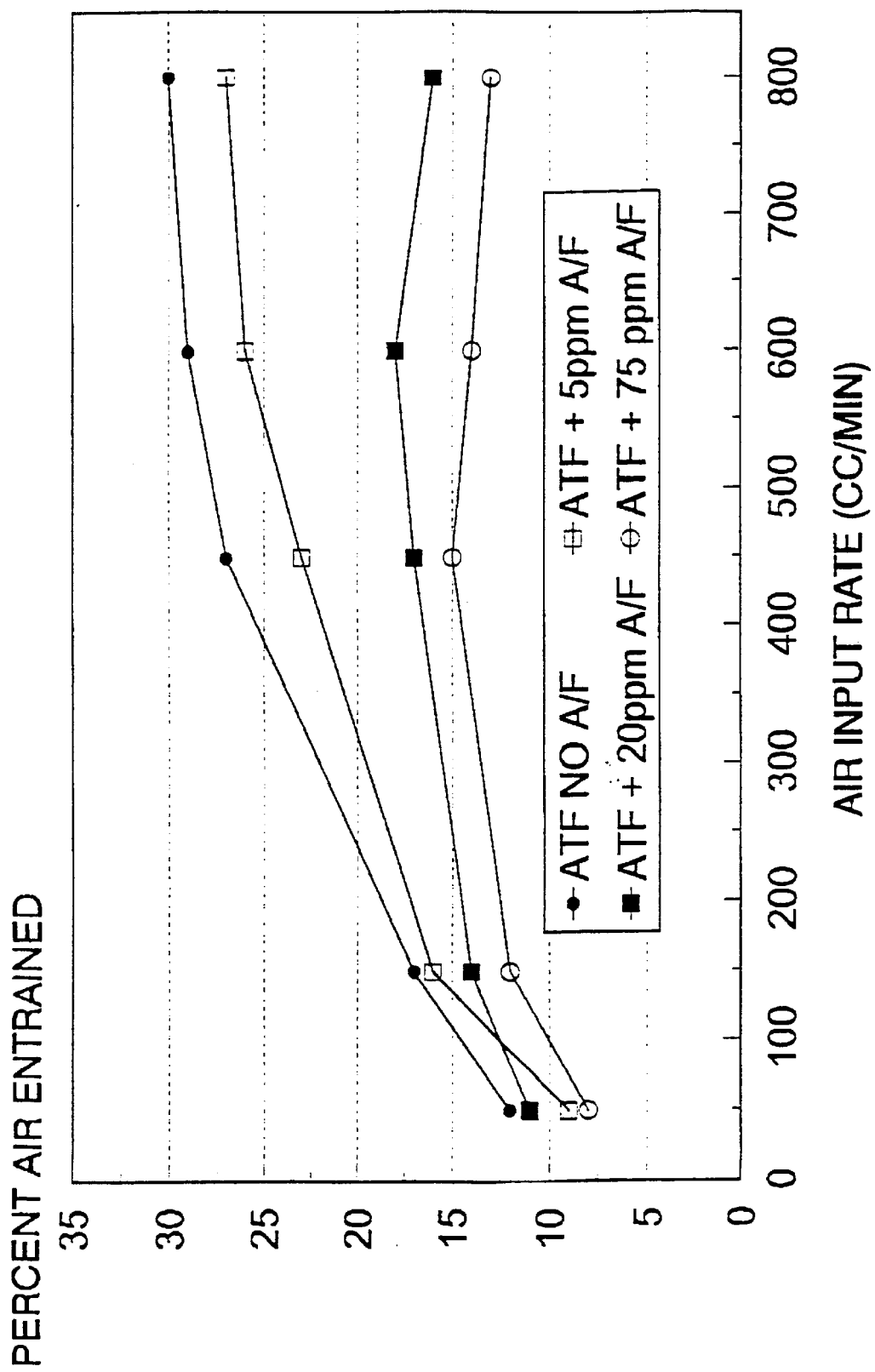
FIG. 2 is a graph showing the percent of air entrained versus the air input rate for different compositions of ATF obtained using an apparatus according to this invention.

FIG. 2 shows a graph of the percent of air entrained versus the air input rate for four different formulations of ATF; ATF without any antifoamant, ATF with 5 ppm antifoamant, ATF with 20 ppm antifoamant, and ATF with 75 ppm antifoamant. The sampling was performed according to the method described above. The graph shows that the apparatus according to the subject invention can be used to accurately differentiate between liquids of differing air entrainment characteristics.

EXPERIMENTAL DATA

Example 1

An apparatus in accordance with FIG. 1 was constructed using stainless steel components. The reservoir had a capacity of 24 liters; the pump had a capacity of 15 liters per minute. Into the reservoir of the test apparatus was placed approximately twelve liters of an automatic transmission fluid prepared without any anti-foam additive. The fluid was heated to 90° C. while being circulated via the pump. Once the temperature stabilized, the control valve was adjusted to give a system pressure of 90 psi. Introduction of air into the suction inlet of the pump was begun at a rate of 50 cc/min. After several minutes a sample was withdrawn and the total volume recorded. When all of the air had been released from the sample the volume of liquid remaining was again recorded. The difference between these two numbers is the volume of air entrained. Percent air entrainment is calculated by dividing the volume of air entrained by the total volume of the sample collected. This procedure was repeated at air introduction rates of 150, 450, 600 and 750 cc/min. The data obtained are shown in FIG. 2 as "ATF NO A/F".

Three samples of the same automatic transmission fluid were then treated with different amounts of a fluorosilicone antifoamant available as FS 1265 from Dow Corning (generically known as Poly-3,3,3-trifluoropropylmethylsiloxane having a viscosity of 300 mm$^2$/sec at 25° C.), which is known to modify both the foaming and air entrainment properties of the lubricant. The three fluids contained 5, 20 and 75 ppm of the antifoamant (A/F), respectively. The procedure above was repeated with each of these fluids. The data obtained in these evaluations are also shown in FIG. 2.

This data demonstrates that the apparatus is capable of producing different levels of air entrainment in lubricants with varying air introduction rates, and is also capable of quantifying the effect of additives on the air entrainment characteristics of lubricants.

Example 2

Three automatic transmission fluids of known transmission air entrainment behavior were evaluated using the apparatus shown in FIG. 1. The procedure used for these evaluations was as follows. Approximately four liters of test fluid were placed in the apparatus reservoir. The pump was started and the rotameter adjusted to meter 170 cc/min of air into the conduit. Heat was applied until fluid temperature reached 90° C. and then maintained. Once the fluid temperature had stabilized the control valve was adjusted to give a pressure of 25 psi in the conduit (recirculating loop). After a brief stabilization period, approximately 10 minutes, five samples were taken by opening the sampling valve five times for 11.6 seconds each time. This is done to purge the sampling outlet. With a clean 250 cc graduated cylinder in place at the sampling outlet an 11.6 second duration sample is collected by triggering the sampling timer. Immediately upon the conclusion of fluid flow from the sampling tube the volume of air/fluid mixture is recorded. The volume of air/fluid mixture is then recorded after 10 seconds, 30 seconds, 1 minute and two minutes. The sampling procedure is repeated two more times to give a total of three samples, and three sets of data.

ATF-1 is known to have excellent transmission performance giving very low air entrainment, ATF-2 is acceptable, and ATF-3 is unacceptable and entrains large amounts of air in an operating transmission. The data obtained are shown in Table 1.

TABLE 1

| Fluid | Percent Air Entrained | | | | |
|---|---|---|---|---|---|
| | Run 1 | Run 2 | Run 3 | Average | Std. Dev. |
| ATF-1 | 3.5 | 5.0 | 7.3 | 5.3 | 1.9 |
| ATF-2 | 10.5 | 11.3 | 13.7 | 11.8 | 1.7 |
| ATF-3 | 13.5 | 14.3 | 13.0 | 13.6 | 0.7 |

The results in Table 1 show that the apparatus of this invention is capable of discriminating between good and bad performing fluids and ranking them in accordance with their transmission performance. Thus, this apparatus which closely mimics the operation of the fluid system of a transmission, along with the sampling techniques arrived at, constitute a unique and accurate method for determining the air entrainment characteristics of a lubricant.

What is claimed is:

1. An apparatus for determining the gas entrainment characteristic of a liquid comprising:
    a liquid reservoir;
    a conduit having an inlet and two outlets connected to the liquid reservoir so as to form a recirculating loop for the liquid in the liquid reservoir, wherein the first outlet discharges liquid above the surface of the liquid in the liquid reservoir, and the second outlet discharges liquid below the surface of the liquid in the liquid reservoir immediately next to the inlet of the conduit;
    a pump for moving the liquid through the conduit; and
    a means for admitting gas into the conduit.

2. The apparatus of claim 1, wherein the liquid is a lubricant.

3. The apparatus of claim 2, wherein the lubricant is automatic transmission fluid.

4. The apparatus of claim 1, further comprising a pressure control valve downstream from the pump to control the pressure in the portion of the conduit between the pump and the valve.

5. The apparatus of claim 1, further comprising a sampling valve disposed downstream from the pump.

6. The apparatus of claim 5, wherein the sampling valve is a solenoid valve capable of being controlled by a timer.

7. The apparatus of claim 1, further comprising a means to heat the liquid.

8. The apparatus of claim 1, wherein the pump is a vane pump.

9. The apparatus of claim 1, wherein the means for admitting gas into the conduit comprises a metered air injection system immediately upstream of the pump.

10. A method for determining the gas entrainment characteristics of a liquid comprising,
    recirculating the liquid from a reservoir through a conduit by a pump, wherein the conduit has an inlet and two outlets connected to the liquid reservoir so as to form a recirculating loop for the liquid in the liquid reservoir, wherein the first outlet discharges liquid above the surface of the liquid in the liquid reservoir, and the second outlet discharges liquid below the surface of the liquid in the liquid reservoir immediately next to the inlet of the conduit;
    injecting gas into the conduit to mix with the recirculating liquid; and
    sampling the liquid.

11. The method of claim 10, wherein the liquid is a lubricant.

12. The method of claim 11, wherein the lubricant is automatic transmission fluid.

13. The method of claim 10, wherein the liquid is recirculated at a controlled temperature.

14. The method of claim 10, wherein the liquid is recirculated at a controlled pressure above atmospheric pressure through a portion of the conduit.

15. The method of claim 10, wherein the gas is injected at a controlled metered rate immediately upstream of the pump.

16. The method of claim 10, wherein the liquid is sampled downstream from the pump at predetermined time intervals.

17. The method of claim 16 wherein the sampling is performed using a solenoid valve.

* * * * *